United States Patent [19]
Zelenjuk et al.

[11] Patent Number: 5,760,377
[45] Date of Patent: Jun. 2, 1998

[54] HEATING ELEMENT OF ELECTRICAL HEATER

[76] Inventors: Jury Iosifovich Zelenjuk, ulitsa Vokzalnaya, 5, kv. 232; Nikolai Evgenievich Peskov, ulitsa Kultury, 10/11, kv.2; Gennady Konstantinovich Piletsky, ulitsa Dzerzhinskogo, 24/1, kv.20; Evgeny Alexeevich Stroev, ulitsa Mayakovskogo, 22, kv.24, all of Ryazan, Russian Federation

[21] Appl. No.: 505,224

[22] PCT Filed: Dec. 14, 1993

[86] PCT No.: PCT/RU93/00301

§ 371 Date: Aug. 14, 1995

§ 102(e) Date: Aug. 14, 1995

[87] PCT Pub. No.: WO95/16414

PCT Pub. Date: Jun. 22, 1995

[51] Int. Cl.⁶ .......................... H05B 3/44; H05B 3/10
[52] U.S. Cl. .......................... 219/544; 219/553
[58] Field of Search ..................... 219/538, 542, 219/544, 546, 548, 549, 552, 553, 528, 211, 457, 464

[56] References Cited

U.S. PATENT DOCUMENTS

| | | |
|---|---|---|
| 3,524,965 | 8/1970 | Arron . |
| 3,904,850 | 9/1975 | Johnson ................ 219/544 |
| 4,063,069 | 12/1977 | Peeri . |
| 4,455,481 | 6/1984 | Van Hoof et al. .......... 219/522 |
| 4,628,188 | 12/1986 | Andreason ............... 219/528 |
| 4,665,308 | 5/1987 | Courvoisier et al. ....... 219/544 |
| 4,954,676 | 9/1990 | Rankin .................. 219/528 |
| 4,983,814 | 1/1991 | Ohgushi et al. ........... 219/544 |

FOREIGN PATENT DOCUMENTS

| | | |
|---|---|---|
| 1038891 | of 0000 | United Kingdom . |
| 1053170 | of 0000 | United Kingdom . |
| 2141029 | of 0000 | United Kingdom . |

*Primary Examiner*—Teresa J. Walberg
*Assistant Examiner*—Sam Paik
*Attorney, Agent, or Firm*—Ladas & Parry

[57] ABSTRACT

A heating element of an electric heater comprising an envelope, having a mass $M_o$ and a surface with an area $S_o$, and a heater in the form of an electrically insulated heating wire, said wire being disposed in said envelope and having a mass $M_H$ and a surface with an area $S_H$. The mass and the surface area of the heating wire and the mass and the surface area of the envelope are related by the relationships $0.1 < M_H/(\lambda M_o) < 0.3$ and $0.8 < S_H/S_o < 0.9$ where $\lambda$ denotes the coefficient of heat transfer of the material of the envelope.

2 Claims, 1 Drawing Sheet

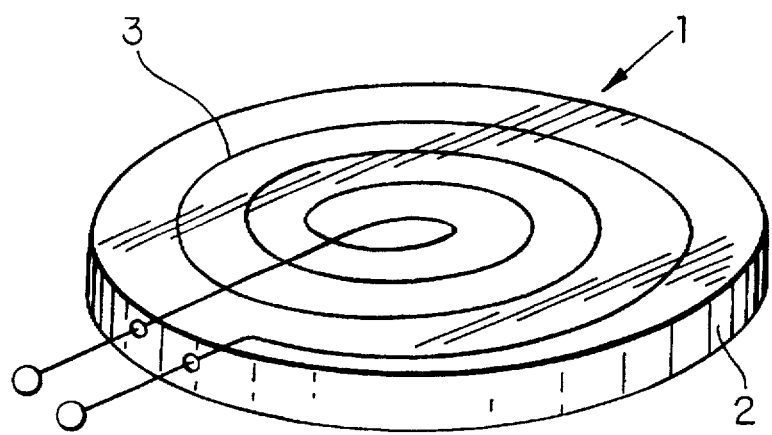

HEATING ELEMENT OF ELECTRICAL HEATER

TECHNICAL FIELD

The present invention relates to instruments for physiotherapy, namely—the heating element of an electrical heater usable for local heating to a temperature not exceeding 45° C. and intended for the therapeutic treatment of various diseases for instance, in rhinolaryngology.

PRIOR ART

The main element of currently known electrical heaters is a heating element adapted to be connected to a current source, said heating element being substantially an envelope, usually flat, which accomodates an electric heating apparatus made from conducting material, generally insulated wire (U.S. Pat. No. 4,614,189, nat. cl. 128–380, 1984; GB Patent No. 1038891, ICI A61F 7/00, 1986). Said wire is represented by constantan, manganin or Ni—Cr alloy which show a relatively high specific resistance of 0.49, 0.43 and 1.1 ohm.mm$^2$/m, respectively, and considerable elasticity. These indices negatively affect the operation characteristics of the heating element and adaptability to manufacture thereof, especially in making miniature heating elements designed for the initial heating of limited portions. For example, during manufacture there arises, due to elasticity inherent in said materials, difficulties in forming the heating wire and what is more, highly complicated is uniform distribution of wire in the body of the envelope of the heating element. Irregularity of the wire distributed results in local overheating, thus worsening said operation characteristics, reducing the operating life. For the manufacture of miniature heating elements and reducing their cost of manufacture it is desirable to use wires having the minimum cross section, and along with this, given such small cross sections there originates the danger of overheating, because of a high resistance of wires, and also of fusion or failure of said heating element envelope. To avoid such overheating, use is made of a heat resistant heat insulated material, usually asbestos, a factor that brings about the increased overall dimensions and mass of the heating element. So one has to admit that conventional heating elements have a rather low coefficient of heat transfer per unit mass of the heating element.

And it should be noted that the use of wires of said materials with a special heat-insulating coat, say, special varnish did not contribute to achieving satisfactory results because of unreliable coating due to the bad adhesion of this coating with said materials of wire.

SUMMARY OF THE INVENTION

It is the principal object of the present invention to select such parameters of a heating wire and the envelope of a heating element such that this heating element has a higher coefficient of heat transfer per unit mass than available heating elements and is more adaptable to streamlined production as well.

The task set is solved owing to the fact that the heating element having an envelope and a heating wire accomodated therein according to the invention, the mass and area of the envelope and heating wire are selected from the ratio:

$m_H = \lambda m_o$ and $0.8 < S_H/S_o < 0.09$ wherein $m_H$ denotes mass of a heating wire, $m_o$ denotes mass of an envelope, $S_H$ denotes area of a conductor of the heating wire, $S_o$ denotes area of one surface of the envelope and $\lambda$ denotes the coefficient of heat transfer of the material of the envelope $K = m_H/(\lambda \cdot m_o)$ wherein K is $0.1 < m_H/(\lambda \cdot m_o) < 0.3$ An electric current conductor is made from flexible material having specific resistance not exceeding 0.02 ohm.mm$^2$/m, say, copper.

If the area of a heating wire is below 0.8 of the area of an envelope, no warm-up is ensured up to the required temperature and if it is over 0.9 of the area of the envelope, adaptability to streamlined manufacture is upset. With "k" less than 0.1 the required heating up is not assured, and if this value exceeds 0.3 no even warm-up is provided.

With such an embodiment of a heating element, the necessity falls away in the provision of special heat insulating elements and the thickness of such heating elements can be only 2–5 mm, which is remarkably less than that of the existing heating elements having a thickness of about 10 mm for the same heating temperature, for instance, up to 45° C. Such a considerable decrease of overall dimensions greatly expands the range of use of the heating elements.

The claimed heating element enables one to utilize a heating wire formed arbitrarily and even by the wires placed in disorder, which makes it possible to easily manufacture heating elements of a variegated hermetic configuration: round, square, elongated, etc. which likewise markedly enlarges the possibilities of use of the heating element. In addition, the production process of the heating element, is simplified since the wire is distributed within the envelope easily and simply, which can be produced by compression moulding, injection moulding, etc.

The present invention is further elucidated by a description of a concrete but not restricting variant of the realization of the invention.

SUMMARY OF THE DRAWING

FIG. 1 schematically showing a heating element with a partially removed envelope.

DETAILED DESCRIPTION OF THE INVENTION

A heating element designated 1 as a whole comprises an envelope 2 and a heating wire 3 accomodated in this envelope. The heating wire is made of an insulated wire and connected with a cord (not shown) to be connected to a power source. Though the envelope 2 is shown in FIG. 1 in the form of a disk, it, nevertheless, may have other forms, say, a cube, ring, to mention just a few. The material used for the manufacture of the envelope can be represented by any material already known for use in electrical heaters. In particular, for the material of said envelope one can use high-pressure ethylene (HPPE). As the wire we utilized copper wires having a resistivity of 0.0175 ohm.mm$^2$/m and insulating coating from non-conducting varnish. This wire is extremely flexible and its placement in the envelope of any configuration presents no difficulties whatever.

Heating elements are known to provide heating in a range of up to 45° C. and we have established that the most favorable conditions of heat transfer of a heating element are secured with the following ratio of the mass and areas of an envelope and heating wire.

$m_H = k\lambda m_o$, wherein:

$m_o$ denotes envelope mass $m_H$ denotes heating wire mass $\lambda$ denotes coefficient of heat transfer of the material of the envelope, $k=(0.1–0.3) m°C./W$ $S_H=(0.8$ denotes $0.9)S_o$, where $S_H$ denotes area of a heating wire conductor $S_o$—area of one surface of the envelope.

Knowing of the material for the manufacture of the envelope of a heating element and considering the latter's intended purpose, which makes it possible to specify its area and thickness one can easily determine the mass of the heating element and its area, whereby to calculate the diameter and length of the wire.

It has been established copper can be substituted with other materials, but whatever the case, specific resistance should not exceed 0.2 ohm.mm²/m, inasmuch as with the ratios of masses and areas of an envelope and heating wire the required temperature conditions fail.

The claimed heating element is adapted to streamlined manufacture: a heating element can easily be formed and distributed inside an envelope, in a disordered form (no strict determination of the form of the heating element is required), since the rigidity characteristics of an insulated wire of plastic materials allow its repeated bending and the mechanical contact of separate parts thereof. The envelope can be produced by casting this or that plastic, simultaneously disposing therein the heating element as an insert.

A comparison of the claimed heating element of a heater with the prior art taken as prototype shows that the claimed element has improved operating characteristics: a comparatively larger surface of heat radiation with a small mass of the heating element; great uniformity of radiation with a low supply voltage; a comparatively high service life explained by the uniformity of radiation by the surface of the body of the element. Besides, the construction of the claimed heating element is more adaptable to streamlined manufacture as permitting using the material of the envelope represented by plastic masses having a comparatively low heat transfer which well yield to compression moulding, injection moulding and as the materials of the wire of the heating element of flexible material with low resistivity.

The construction provides for the presence of not only a thermal but also a magnetic field, which increases a medical effect (low electric resistance, a comparatively strong current, the high level of a magnetic field).

We claim:

1. A heating element of an electric heater, comprising:

an envelope, having a mass $M_o$ and a surface with an area $S_o$, a heater in the form of an electrically insulated heating wire, said wire being disposed in said envelope and having a mass $M_H$ and a surface with an area $S_H$, wherein said mass and said surface area of said heating wire and said mass and said surface area of said envelope are related by the relationships $0.1 < M_H/(\lambda M_o) < 0.3$ and $0.8 < S_H/S_o < 0.9$ where $\lambda$ denotes the coefficient of heat transfer of the material of the envelope, and the heating wire is made of a flexible material having a specific resistance of less than 0.02 Ohm mm.kV/m.

2. The heating element of claim 1, wherein copper is used as the material of the heating wire.

* * * * *